(12) United States Patent
Lentini et al.

(10) Patent No.: US 6,177,092 B1
(45) Date of Patent: Jan. 23, 2001

(54) SELF-FOAMING CLEANSING SYSTEMS

(75) Inventors: Peter J. Lentini, Bayside, NY (US); Jules Zecchino, Closter, NJ (US)

(73) Assignee: Color Access, Inc., Melville, NY (US)

( * ) Notice: Under 35 U.S.C. 154(b), the term of this patent shall be extended for 0 days.

(21) Appl. No.: 09/189,827

(22) Filed: Nov. 10, 1998

(51) Int. Cl.$^7$ .................................................. A61K 7/00
(52) U.S. Cl. ................................................. 424/401; 424/44
(58) Field of Search ................................................. 424/49

(56) References Cited

U.S. PATENT DOCUMENTS

| | | | | |
|---|---|---|---|---|
| 3,729,553 | * | 4/1973 | Gold et al. | 424/44 |
| 4,487,757 | * | 12/1984 | Kiozpeoplou | 424/7.1 |
| 5,455,035 | | 10/1995 | Guerrero et al. | 424/401 |
| 5,855,871 | * | 1/1999 | Masters et al. | 424/49 |

FOREIGN PATENT DOCUMENTS

| | | |
|---|---|---|
| 0 745 665 | 4/1996 | (EP) . |
| 2 738 148 | 7/1997 | (FR) . |
| 2 293 157 | 3/1996 | (GB) . |

OTHER PUBLICATIONS

Brose, E., et al., "Chemical Leavening Agents", Aug., 1996, pp. 13–24, Chemische Fabrik Budenheim Rudolf A. Oetker.

* cited by examiner

*Primary Examiner*—Shelley A. Dodson
*Assistant Examiner*—Konata M. George
(74) *Attorney, Agent, or Firm*—Kenyon & Kenyon

(57) ABSTRACT

The present invention relates to a system that is self-foaming. The self-foaming system has at least two components that are maintained in separate containers. The components produce carbon dioxide when they commingle with each other upon being dispensed from their individual containers. The components are stored separately by being partitioned in separate containers or a container having a chamber for each of the components. The self-foaming system of the present invention has cleansing and cooling properties. The system is mild yet non-irritating because it cools and cleans deeply without interfering with the natural barriers of the skin.

12 Claims, No Drawings

SELF-FOAMING CLEANSING SYSTEMS

FIELD OF THE INVENTION

The present invention relates to self-foaming systems. In particular, the invention relates to self-foaming systems having at least two components that effervesce when they are dispensed and that are cleansing, cool, and refreshing to the skin.

BACKGROUND OF THE INVENTION

Typical cleanser formulations are designed to effectively and efficiently remove previously applied face powder, rouge, foundation bases, eyeshadow and lipstick. Surfactants are also particularly useful in removing waterproof makeup. In addition, cleansers remove dirt and oil that accumulate on the skin or in the hair. To achieve this, commercial facial cleansers, usually in the form of a gel, lotion or cream, use surfactant ingredients. Further, a refreshing feeling is experienced when the surfactant is in contact with water because it generates a bubbly foam. Unfortunately, many surfactants are drying to the skin and/or are irritating to user. Because they contain surfactants, many cleansers cannot be routinely used in or in some instances even around the eye area.

Surfactants can interfere with the natural protective lipid barrier of the skin. There are two sources of skin surface lipids making up this important barrier: the sebaceous glands and the epidermis. Lipids are a diverse croup of compounds, comprising triglycerides, diglycerides, ceramides, free fatty acids, wax esters, cholesterol and cholesterol esters, and squalene. The quantity and composition of the skin surface lipids differ from place to place on the body, and may to some extent be related to the number of sebaceous glands in a given area of the skin. The condition of the skin surface lipids may also be affected by an essential fatty acid deficiency. Additionally, the lipid barrier can be diminished by exposure to harsh detergents or soaps containing surfactants. Therefore, cleansers are desired which do not interfere with the lipid barrier of the skin, but which clean thoroughly and, feel cool and refreshing.

Another desirable characteristic of cleansing products is the refreshing feeling derived from a cooling sensation on the skin. To achieve a physiological cooling effect on the skin, it is known in the prior art to use, for example, menthol or other similar low volatile compounds. Other compositions used include acyclic secondary and tertiary sulphoxides and sulphones, p-menthane and its derivatives. However, these compositions have a strong odor and are not desirable for use on the skin. Therefore, a less traditional form is needed that will provide a refreshing and cooling feeling that is pleasant to use.

Consumers of cleansers not only desire a product that cleans deeply, they desire a product that "feels" like it cleans deeply. This feeling is achieved when a cleanser product is cool, refreshing and tingly or bubbly during its use. The present invention provides a self-foaming system that produces a cooling sensation, cleans deeply, and "feels" like it cleans deeply but does not interfere with the delicate lipid barrier of the skin.

SUMMARY OF THE INVENTION

The present invention relates to a cosmetic or pharmaceutical self-foaming system for application to the skin or the hair. The system comprises, as separate aqueous components, at least two components: an acid component and an alkali metal bicarbonate component. The acid component is either an organic acid with no greater than 8 carbon atoms or an inorganic acid. Examples of acids include but are not limited to citric acid, ascorbic acid, tartaric acid, gluconic acid, malic acid, acid potassium bitartrate, acid sodium citrate, phosphoric acid and acid phosphate and pyrophosphate salt, such as monosodium phosphate and disodium pyrophosphate, salicylic acid, lactic acid, as well as other salts of these acids. The bicarbonate component can be sodium bicarbonate or potassium bicarbonate. The two components are each combined with a cosmetically or pharmaceutically acceptable carrier. To use the system, the components are dispensed and applied to the surface to be treated, such as the skin or the hair. Upon commingling with each other, the acid and bicarbonate components release carbon dioxide In one embodiment, the present invention relates to a unitary package for dispensing the cosmetic or pharmaceutical self-foaming cleansing. The package for the cleansing system has at least two individual, separate non-communicating chambers. Each chamber holds a different reactive component and has an opening for dispensing the components. The non-communicating chambers keep the components inert while they are separate and until they are dispensed from the chambers. When the components are combined as described above, they produce carbon dioxide and generate an effervescent cleansing experience. The present invention includes a method of cooling the skin which comprises applying an effective amount of the cosmetic or pharmaceutical self-foaming system.

The self-foaming cleansing system is advantageous because it is gentler to the lipid barrier of the skin than a traditional cleanser containing a large percentage of surfactants, yet the system cleans deeply and has a tingly, bubbly and cool feel when used. The cleanser helps prevent the development of dry skin and other undesirable results that can occur when using, for example, a cleanser with a large amount of surfactants.

DETAILED DESCRIPTION OF THE INVENTION

The present invention is cosmetic or pharmaceutical systems having at least two components that commingle and effervesce upon being dispensed simultaneously from separate containers. An important aspect of the present invention is its ability to provide cleansing and cooling properties. Accordingly, the present invention includes a cleansing system and a method for cooling the skin which comprises applying the self-foaming system to the skin. Another feature of the present invention is that the effervescent property of the system occurs at a particular time when the user applies it to the skin or the hair.

Foaming action is primarily desirable at the time the system is applied to and during use on the skin or the hair. After the components of the system are dispensed from their respective containers or chambers, they are applied to the skin or the hair where effervescence is desired immediately upon contact. In contrast, before applying the components of the system to the skin, effervescence is not necessary. Likewise, after using the system on the skin or the hair, effervescence is no longer needed because use of the system is concluded and the components of the system are removed from the skin or the hair by rinsing or some other similar action. Therefore, the timing involved in creating the effervescent property is an important aspect of the system.

Effervescence is a widely used, desirable and useful property of many commercial products that makes a product feel tingly or bubbly. Typically, the effervescent property of these products is based on the generation of carbon dioxide gas. The creation of carbon dioxide gas involves reacting an acid with bicarbonate. Bicarbonate is a relatively common household product also known as baking soda. In aqueous solution, bicarbonate releases carbon dioxide gas unless it is stabilized. Generally, this reaction proceeds rapidly because the acid and the alkaline neutralize each other. As the reaction progresses toward completion the effervescence diminishes and eventually ends when the reaction is complete.

It is known in the prior art to use sodium bicarbonate in personal care products. For example, a sodium bicarbonate effervescent system is used in a toothpaste product after overcoming challenges to make a product that is acceptable to the user. U.S. Pat. No. 4,487,757, incorporated herein by reference, discloses how to make a toothpaste container containing a baking soda toothpaste that overcomes the challenges of water solubility, salty taste, stability in the container, and its appearance when dispersed. An example of a two component foaming system is disclosed in U.S. Pat. No. 5,455,035 which provides for a surface active material in a cosmetic composition by neutralizing an organic acid surfactant precursor having 10 to 20 carbon atoms, and an alkaline neutralizing agent to provide the surface active material.

An important feature of the present invention is its ability to provide a self-foaming system that is substantially non-irritating. In contrast to other foaming systems, which require the use of surfactants or other irritating agents to achieve the desired foaming property, the present invention achieves this by carbon dioxide generation in situ upon application. When use of the cleansing system is desired, the components are combined. The components mix together as they are poured out of their respective chambers and they react to create carbon dioxide gas. Accordingly, at least one of the components is an alkali metal carbonate or bicarbonate.

The alkali metal bicarbonate can be, for example, sodium carbonate, sodium bicarbonate or potassium bicarbonate. In a preferred embodiment, the bicarbonate component is dissolved in an aqueous solution. The alkali metal bicarbonate may totally dissolved, or it may be supersaturated. Effervescence occurs only when the separate components of the system are combined in the presence of water. However it is within the scope of the present invention to utilize other solutions including non-aqueous solutions (i.e., for use in anhydrous products). In the case of an anhydrous product, water can be added to produce effervescent action or, the anhydrous product can be added to water. For example, the present invention may be in the form of a sachet containing the components of the system that is added to a bath of water.

At least one of the other components reacts with the bicarbonate component to yield carbon dioxide gas. This other component can be an acid having 1 to 8 carbon atoms and being water soluble. The acid can be a carboxylic acid. Specific examples of the acid component include but are not limited to citric acid, ascorbic acid, tartaric acid, lactic acid, salicylic acid, gluconic acid, malic acid, fumaric acid and salts thereof. Examples of acid sodium, potassium, and calcium salts include but are not limited to acid potassium tartrate, acid potassium bitartrate, calcium phosphate, sodium aluminum phosphate, sodium aluminum sulfate, monosodium phosphate, disodium pyrophosphate, calcium lactate, calcium sulfate, calcium phosphate, sodium aluminum phosphate, sodium aluminum sulfate, monosodium phosphate and disodium pyrophosphate. Preferably, the acid is a citric, lactic or salicylic acid, or a combination thereof.

The acid component can also include leavening agents, such as those disclosed in Brose, E., et al., "Chemical Leavening Agents", (Chemische Fabrik Budenheim Rudolf A. Octker 1996), pps. 13–24. Examples of leavening agents can include but are not limited to acid sodium, potassium, and calcium salts of citric acid and tartaric acid, ortho phosphoric acid, and pyrophosphoric acid. Other specific leavening agents include, calcium lactate, calcium sulfate, sodium acid pyrophosphate, monocalcium phosphate monohydrate, anhydrous monocalcium phosphate, dicalcium phosphate dihydrate, sodium aluminum phosphate, sodium aluminum sulfate, acidic potassium tartrate, glucono delta lactone, citric acid, tartaric acid, fumaric acid and lactic acid.

The two reactive components can be dispensed from physically separate packages or from a unitary package with chambers. The components of either type of packages can be applied simultaneously or substantially simultaneously to the skin, where they commingle and react. The term "substantially simultaneously" as used herein refers to application of each of the components within temporal proximity to one another not longer than the stability of the initially applied component. In other words, there may be two steps to applying the two reactive components. In the first step, one component is applied to the skin and in the second step, the other component is applied over the first component within a period of time less than the stability time of the first component. The components are, thus, applied substantially simultaneously such that commingling occurs when the second component is applied on top of the first component. For example, one package can contain a cosmetic composition in the form of a moisturizer containing the acid component which is applied to the skin. The other package can contain another cosmetic composition in the form of a foundation containing the bicarbonate component which is applied on top of the previously applied moisturizer. Commingling occurs when the foundation is applied over the layer of the moisturizer on the skin.

When the components are applied in two steps, the time of applying the second component and commingling it with the first component is limited by the stability of the first component that is applied to the skin. The stability of the first component can depend on external factors such as humidity, temperature, and other factors as, for example, contact with materials or agents that alter the stability of the component or even remove the component from the surface of the skin. However, under conditions that do not alter the stability of the first component and/or do not cause the first component to be removed from the skin, the amount of time within which the second component can be applied to the skin and still result in commingling with the first component sufficient to bring about cooling and effervescence is from about 1 to about 60 minutes.

Preferably, the components of the system are dispensed from a unitary package. The package has at least two separate, non-communicating chambers for containing each of the different reactive components and an opening for dispensing the components. The opening of the chamber is designed to permit substantial simultaneous dispensing and commingling of the reactive components (i.e., the components merge immediately as they flow out of their individual chambers.)

Non-communicating containment keeps the components in close proximity to one another; but, prevents them from coming into contact with one another until the desired time of their use. For example, the bicarbonate component is kept physically separate from the acid component to prevent premature interaction. The bicarbonate component is stable and non-effervescent while it is partitioned separately from the acid component. Therefore, the components remain inert while they are contained in separate chambers. At the desired time of use, the components are dispensed from their respective chambers. As they flow out, they commingle and react with each other to create carbon dioxide gas and consequently, to create the effervescent property of the system.

The form of the package can be a tube, a bottle, an aerosol or pressurized gas activated can or other suitable container. The unitary package may also have multiple chambers within, if there are more than two components. For example, a tube can be molded to have more than one partitioning wall inside to produce multiple chambers within the tube.

In a preferred embodiment of the present invention, the self-foaming system comprises an alkali metal bicarbonate component and an organic acid component having not greater than 8 carbon atoms. More preferably, the alkali metal bicarbonate of the system is sodium bicarbonate and the organic acid is citric acid. The degree of effervescence (i.e., the longevity and intensity) obtained when the sodium bicarbonate and the citric acid components come into contact with each other and react, after being dispensed from their respective containers, can be adjusted by changing the ratio of these components to one another and the relative amounts of the two components present in the system.

To intensify and lengthen the duration of the reaction and consequently, the effervescent property derived from carbon dioxide generation, each of the components of the system may be present in an amount from about 0.5 to about 50 percent, by weight of each component, preferably about 1 to about 20 percent, and more preferably about 1 to about 10 percent. The components are present in the system in a ratio of 1.0:0.5 to 0.5:1.0 by weight of each component; more preferably 1:1. However, the ratio can be adjusted according to the concentration of the components. Similarly, the cooling sensation created by the system varies in intensity and longevity in a manner comparable to that of the self-foaming action.

The degree of effervescence can also be enhanced during application to the skin or the hair. For example, agitation such as rubbing, circular type motion, or other similar types of action by the user during application of the product augments the degree of effervescence experienced while applying the system to the skin or the hair. Some of the carbon dioxide gas produced at atmospheric pressure remains in solution and can settle in the skin or hair as it is applied. These phenomena not only help prolong the degree of effervescence but also allow the system to be used as a mousse in a nonpressurized package (i.e., the package does not require the use of propellants as used with an aerosol can).

In one embodiment of the present invention, the system is used as a cleanser. The carbon dioxide generated itself has cleansing properties, and the self-foaming and cooling aspects of the reaction accomplish what surfactants are specifically needed for in many formulations. The surfactant, similarly, may be used in any amount appropriate for the chosen surfactant. However, preferably, because the surfactant is not required in large amounts in the present invention, the surfactant will generally be present in smaller quantities, in an amount of no greater than 20% by weight of the total composition; more preferably no greater than 10%. The quantity of surfactants used in the system is reduced in comparison with the quantity of surfactants used in typical foaming products. Typically, a foaming product uses about 40 to about 60% surfactant by weight of the total composition. But, the systems of the present invention provide self-foaming action using considerably less than that amount (i.e., about 20%). Therefore, the system of the present invention can reduce the quantity of surfactant needed by about two-thirds to one-half of the quantity used in standard self-foaming products. In a preferred embodiment, the amount of surfactant added is no greater than 10% by weight of the total composition.

The surfactant may be of any type. In the event that it is desired to include a surfactant in the system, the type of surfactant incorporated in the formulation will depend on its intended purpose. For example, surfactants may be used to assist in wetting the skin or the hair. The properties of surfactants may also aid in promoting the reaction between the bicarbonate and the acid components thereby increasing the effervescence of the product. The type of surfactant selected will also be one which does not interfere with the production of carbon dioxide gas. Additional surfactants may be included in any or all of the components of the system. However, selection is further limited by the compatibility of a given surfactant with the component into which it is incorporated. Accordingly, the surfactants employed may be any that are traditionally used for cosmetic or pharmaceutical purposes, and may be selected from nonionic, anionic, cationic, amphoteric surfactants, or mixtures thereof, the identities of which are well known to those skilled in the art. Preferably, however, the surfactant is nonionic or anionic. Further, if the system is intended for use in close proximity to the eye area or other sensitive areas, it is preferred that the surfactant be a mild surfactant, such as LIPO-PEG-2DL or disodium cocoamphodiacetate (Miranol).

Each of the components can be formulated with a variety of cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. It will be apparent to the skilled artisan that the selected carrier must be compatible and relatively inert with respect to the reactive components. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co., Easton, Pa., 1990. Further, the carrier may be in any form appropriate to the mode of delivery, for example, solutions, colloidal dispersions, emulsions (oil-in-water or water-in-oil), suspensions, creams, lotions, gels, foams, mousses, sprays, slurries and the like.

Other potentially useful additions to the self-foaming system include emollients, humectants, fragrances, preservatives, and buffers. Such materials are routinely used in cosmetic products, and listings of appropriate materials can be found, for example in the International Cosmetic Ingredients Handbook, Third Edition, 1996 ("CTFA").

The self-foaming systems of the present invention are useful in products for the skin or the hair such as cleansers, conditioners, suncare products, makeup products, and the like. More specific examples include shampoos or rinsing products. When the system is used in a rinsing product, it can be applied before or after shampooing, before or after dyeing or bleaching, before or after permanent waving or hair-straightening, or it can be applied after using a hairdressing, a hair dyeing or bleaching product, or a conditioning or hair-setting gel that is temporarily used on the hair. Yet another form that the system can take is that of a shaving gel.

In one embodiment, however, the system is used primarily for its cooling effects, and not as a cleanser. For example, the system can be advantageously used as the base of a foundation or sun-care product. These types of products, when applied in hot and/or humid weather conditions, can feel uncomfortable on the skin. The application of the system under such conditions will provide a cooling effect, in addition to the other intended effect of the product and avoid some of the discomfort often associated with more traditional products of this type. When the cooling effect is the primary intention of the system, a water-in-silicone combination is preferred.

In a particularly preferred embodiment, however, the system is used for removing dirt, oil, makeup, and other impurities from the skin or the hair. For example, the systems can be used in a cleanser or toner product for the face or in a product for application to the body. As already noted, because of the ability to effervesce by means of carbon dioxide gas generation, the self-foaming systems are mild and do not interfere with the natural protective lipid barrier of the skin. In addition, carbon dioxide generation augments the cooling and cleansing properties of the system.

In addition, the systems can be used for delivery of cosmetic or pharmaceutical topically therapeutic active agents to the skin for the treatment and/or amelioration of various skin conditions. Accordingly, the self-foaming systems of the present invention may also comprise useful active ingredients, for the purposes of treating both the skin and the hair. Useful active ingredients include, but are not limited to antioxidants, antimicrobials, sunscreens, analgesics, anesthetics, anti-acne agents, antidandruff agents, antidermatitis agents, antipruritic agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antihistamine agents, skin lightening agents, depigmenting agents, wound-healing agents, vitamins, corticosteroids, tanning agents, or hormones. The selection of the active in the formulation is determined by its solubility and/or stability in either oil or water.

The present invention also includes a method of producing the cooling sensation when an effective amount of the components of the system are dispensed and applied to the skin or the hair. When combined with appropriate additional components, the resulting self-foaming systems successfully cool skin surfaces, including around the eyes and lips. Moreover, they clean the skin and remove transfer-resistant cosmetics. All this is achieved while remaining gentle and substantially non-irritating to the user. The cooling effect may also be, in some cases, enhanced by combining the components of the system with an additional cooling agent, for example, menthol. If an additional cooling agent is used, it is present in an amount of no greater than 5 percent of the weight of the total composition.

The invention is further illustrated in the following non-limiting examples:

EXAMPLES

1. The following illustrates a formulation of the present invention:

| Material | Component 1 (% by weight) | Component 2 (% by weight) |
| --- | --- | --- |
| Deionized Water | 90 | 90 |
| Disodium EDTA | 0.05 | 0.05 |
| Glycereth-26 | 2 | 2 |
| Methyl Gluceth | 2 | 2 |
| Polaxamer 184 | 0.4 | 0.4 |
| Potassium Sorbate | 0.1 | 0.1 |
| Fragrance | 0.08 | 0.08 |
| Menthol crystals | 0.02 | 0.02 |
| Polysorbate 20 | 0.15 | 0.15 |
| PPG-5-Ceteth-20 | 0.2 | 0.2 |
| PEG-120 Jojoba Acid and Alcohol | 0.2 | 0.2 |
| Sodium Hyaluronate | 0.1 | 0.1 |
| Sodium bicarbonate | 4.7 | |
| Disodium pyrophosphate | | 4.7 |

The constituents of each component, i.e., Component 1 and Component 2, are added until they are dissolved using a propeller mixer.

What we claim is:

1. A method of cleansing the skin or the hair which comprises applying an effective amount of a cosmetic or pharmaceutical liquid self-foaming system comprising, as separate aqueous elements, an alkali metal bicarbonate component and an acid component, said acid component being selected from the group consisting of an organic acid having a number of carbon atoms not greater than 8 and an inorganic acid, each of said components being contained in a cosmetically and/or pharmaceutically acceptable carrier, said components, when substantially simultaneously dispensed and commingled, reacting with one another to release carbon dioxide.

2. A method of cooling the skin which comprises applying an effective amount of a cosmetic or pharmaceutical liquid self-foaming system comprising, as separate aqueous elements, an alkali metal bicarbonate component and an acid component, said acid component being selected from the group consisting of an organic acid having a number of carbon atoms not greater than 8 and an inorganic acid, each of said components being contained in a cosmetically and/or pharmaceutically acceptable carrier, said components, when substantially simultaneously dispensed and commingled, reacting with one another to release carbon dioxide.

3. A unitary package for dispensing a cosmetic or pharmaceutical liquid self-foaming system, said package containing at least two separate, non-communicating chambers and at least two reactive flowable components, at least one of said reactive components being an acid in an aqueous solution of at least 80 percent, said acid being selected from the group consisting of an organic acid having a number of carbon atoms not greater than 8 and an inorganic acid, at least one of said reactive components being an alkali metal bicarbonate in an aqueous solution of at least 80 percent, each of said chambers containing a different reactive component and having an opening for dispensing said component, wherein said components are capable of reacting with each other when substantially simultaneously dispensed and commingled to produce carbon dioxide, but which remain inert when contained within said separate chambers.

4. The method of claim 1 wherein the alkali metal bicarbonate is a sodium bicarbonate.

5. The method of claim 1 wherein the acid is organic.

6. The method of claim 5 wherein the acid is citric acid.

7. The method of claim 1 wherein the acid is inorganic.

8. The method of claim 7 wherein the acid is selected from the group consisting of pyrophosphoric acid, phosphoric acid, and sulfuric acid, and salts thereof.

9. The method of claim 8 wherein the salt is calcium sulfate, calcium phosphate, sodium aluminum phosphate, sodium aluminum sulfate, monosodium phosphate and disodium pyrophosphate.

10. The method of claim 1 wherein the acid is a leavening agent.

11. The method of claim 1 wherein the liquid self-foaming system is a toner.

12. The method of claim 2 wherein the liquid self-foaming system is a toner.

* * * * *